United States Patent
Tuunanen

[19]

[11] Patent Number: 6,111,636
[45] Date of Patent: Aug. 29, 2000

[54] DEVICE FOR MEASURING OPTICAL DENSITY

[75] Inventor: Jukka Tuunanen, Helsinki, Finland

[73] Assignee: Labsystems Oy, Helsinki, Finland

[21] Appl. No.: 09/253,972

[22] Filed: Feb. 22, 1999

[30] Foreign Application Priority Data

Apr. 17, 1998 [FI] Finland ................................. 980855

[51] Int. Cl.⁷ .................................................. G01J 1/00
[52] U.S. Cl. ............................................. 356/213; 356/39
[58] Field of Search ............................... 356/36, 39, 419,
356/422, 213, 426, 418; 422/100, 67, 102,
63, 65, 922, 73, 55, 58

[56] References Cited

U.S. PATENT DOCUMENTS

| 4,482,251 | 11/1984 | Saylor . | |
|---|---|---|---|
| 4,580,895 | 4/1986 | Patel | 356/39 |
| 5,112,134 | 5/1992 | Chow et al. | 356/427 |

FOREIGN PATENT DOCUMENTS

| 0 135 303 A3 | 3/1985 | European Pat. Off. | G01N 21/03 |
|---|---|---|---|
| 0217632 | 4/1987 | European Pat. Off. . | |
| 0 273 671 A3 | 7/1988 | European Pat. Off. | G01N 21/25 |
| 0273671 | 7/1988 | European Pat. Off. . | |
| 669 851 A5 | 4/1989 | Germany | G01N 35/02 |
| 42 03 574 A1 | 2/1991 | Germany | G01N 35/02 |
| 4117008 | 11/1991 | Germany . | |
| WO 92/02791 | 2/1992 | WIPO | G01J 1/20 |

OTHER PUBLICATIONS

Patent Abstracts of Japan; vol. 009, No. 259 (P–397), Oct. 17, 1985; JP 60108731; Jun. 14, 1985 abstract.
International Search Report; EP 99 660039; Jan. 20, 2000; E. Navas Montero.

Primary Examiner—Frank G. Font
Assistant Examiner—Tu T. Nguyen
Attorney, Agent, or Firm—Fish & Richardson P.C.

[57] ABSTRACT

The application relates to a device for measuring the optical density of samples arranged in strips on a plate. The device comprises a measurement head (3) moving strip by strip in relation to the plate, said measurement head (3) including a light source (4) and a detector (5). Outside the strips, there is provided a transparent spot (9) or a light-proof spot (10), at which the light source intensity or the background signal can be measured either before or after the strip measurement. By employing the single-channel device according to the invention, it is possible to achieve virtually the same speed level as with a multichannel device. However, the device of the invention can be made remarkably simpler. One single-channel device can also be used for measuring several different plates.

23 Claims, 3 Drawing Sheets

DEVICE FOR MEASURING OPTICAL DENSITY

BACKGROUND OF THE INVENTION

The invention is connected to laboratory technology and relates to a device for measuring optical density, such as a photometer, nephelometer or a fluorometer, for measuring the optical density of several samples placed on one and the same sample plate. The device can be used for instance in clinical laboratories, where analyses are made in large series. The most widely used plate is a so-called microtitration plate, which contains a matrix of 8×12 sample wells in a 9 mm division.

In order to render the sample plate measurement time as short as possible, multichannel devices are produced. For microtitration plates, there are available photometers provided with 8 or 12 channels for measuring one vertical or horizontal strip at a time (for example the analyzers MULTISKAN and EMS Reader MF by Labsystems Oy). Devices with as many as 96 channels have been produced. The total measurement time achieved by means of multichannel photometers is about 5 s. In practice, a sufficiently short measurement time can be considered to be 10 s.

In multichannel photometers, there is needed a number of detectors, optical devices connected to the detectors, as well as preamplifiers, said number corresponding to the number of channels. In order to distribute the light from the light source to the separate channels, there are needed optical devices. Generally it also is necessary to prevent light from flowing between channels during measurements. The processing of parallel measurement results also requires special arrangements. Thus a multichannel photometer necessarily becomes relatively complicated and expensive. In addition, the separate measurement channels are never quite equal, which may lead to harmful errors in accurate measurements.

There also exist single-channel readers for microtitration plates (for example the BIOSCREEN and Auto-EIA analyzers by Labsystems Oy), which are simpler and cheaper in comparison. However, their drawback is a longer measurement time (about 30 s). Although the measurement time need not be an essential factor from the point of view of the overall analysis, users regard the extra delay time as a problem.

The intensity of the light source fluctuates, and this is taken into account in the measurements. A typical stability requirement is of the order 1:1000. In some photometers, the light source intensity is measured only once, prior to the measurement of the samples. Before measurement, these devices must be allowed to be stabilized sufficiently long with the light source switched on. A typical stabilizing time is about 10–30 minutes, which slows down the use of the apparatus. Therefore, some devices are provided with a separate reference channel for observing the fluctuations of the light intensity and for taking it into account when calculating the measurement results. When employing such devices, the measurement can be carried out immediately after the device is switched on. A drawback, however, is caused by the additional arrangements required by the reference channel. The realization of a sufficiently accurate and stabile reference channel also calls for special arrangements.

Changes in the background signal are also taken into account in the measurements. They are caused by the bottom signal of the electronic components (including the detector) which changes as a function of temperature. Background measurement, as close to real-time as possible, is important particularly when measuring high optical densities, and the quality of the background measurement has a direct effect on the scale of the measurement area. A typical requirement for accuracy is of the order 1:100000. Many photometers employ a light interrupter, whereby the light obtained from the light source is interrupted, for instance at a frequency of about 300 Hz. Thus the point of interruption can be used for measuring the background.

GENERAL DESCRIPTION OF THE INVENTION

The present invention relates to a device for measuring optical density according to the appended patent claim 1. A few preferred embodiments of the invention are presented in the rest of the claims.

The device according to the invention comprises a measurement head and plate which are movable in relation to each other, and the measurement is carried out strip by strip. Before or after the measurement of a particular strip, the light source intensity or the background signal is measured from outside said strip.

By employing the single-channel device according to the invention and the principle of measurement applied therein, it is virtually possible to achieve a similar speed level as with a multichannel device. However, the single-channel device can be made remarkably simpler and cheaper than the multichannel device. With one single-channel device, several different plates can also be measured.

DRAWINGS

The appended drawings belong to the detailed description of the invention.

DETAILED DESCRIPTION OF THE INVENTION

Figure 1:
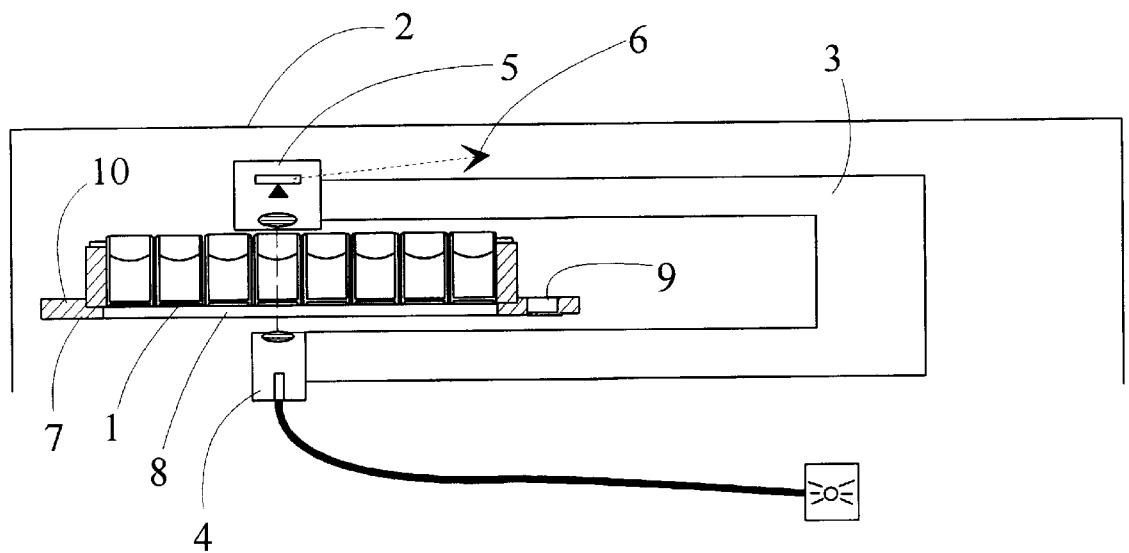
FIG. 1 illustrates a measurement unit of a measurement device according to the invention, as seen from the end.

The sample plate used in the invention contains sample strips, where each strip includes several samples. The optical density of each sample is measured by conducting light into the sample and by measuring the intensity of the light emitted from the sample. In order to realize this, the device comprises a measurement head and a plate, which move in relation to each other. The measurement head is provided with a light source in order to conduct light into the sample, and a detector for receiving the light emitted therefrom. In addition to this, the device is provided with other necessary means, such as means for processing the signals obtained from the detector and for conducting them further, and means for moving the measurement head or the plate.

In practice, the device must include both a transparent area for observing the light source intensity, and a light-proof area for observing the background. In practice the transparent area must be such that the light proceeds through mere air. Light is generally conducted into the sample in vertical direction.

The samples are measured strip by strip and advantageously so, that the measurement head checks the strips by successive to-and-fro motions. In principle, for reading plates with particularly many strips, there can also be used two or more measurement heads, in which case the plate reading time is respectively reduced, but the device becomes more complicated.

Before or after measuring the strip, there is measured the light source intensity or the background. In order to measure the light intensity, outside the strip, preferably on an extension thereof, there is arranged a transparent spot, through which the light to be conducted into the sample enters the detector as freely as possible. In order to measure the background, outside the strip there is respectively arranged a light-proof spot, through which the detector does not catch any light conducted into the sample nor emitted from the sample. Advantageously said spots are located outside the plate and apart therefrom, so that extra space is not needed for them on the plate. The transparent spot is preferably a completely open area located at the side of the plate, via which light passes through mere air from the light source to the detector, in which case only the attenuation caused by air affects the strength of the intensity to be measured. The light-proof spot can be for instance a sector transversal to the strips, located at the side of the plate, or a smaller area. Naturally the measurement head must be able to extend to said spots in order to carry out the measurements.

Most advantageously the device comprises a moving measurement head. In that case the plate may remain completely in place during the whole process of measurement, wherefore it is necessary that the measurement head can be moved both in parallel to the strip and against it, at right angles to the strip. The advantage of a completely stationary plate is that the liquid surface is prevented from rippling along with the plate motions and thus from interfering with the measurement.

The device can also be of a type where the plate moves in the transversal direction of the strip, so that the measurement head need not move, except in the direction of the strip. This type of a structure, composed of two members moving only in one direction, can be made fairly simple. The plate trajectory can also be utilized for inserting the plate into the measurement chamber provided in the device and for removing the plate therefrom. This simplifies the sealing of the measurement chamber. The motion of the plate can also be utilized for opening the hatch provided in the measurement channel. A drawback caused by the moving of the plate is that after motion, the liquid surface may ripple for some time, wherefore a precise measurement cannot be carried out immediately. The extra delay is, however, fairly short, and it is necessary only when proceeding further after the second strip and successive strips. In addition, during the plate transfer, there is time to carry out background or light intensity measurements.

According to a preferred embodiment, the background or the light source intensity is only measured at one end of the strip, in particular so that one is measured at one end, and the other is measured at the opposite end. If the measurement head always reads adjacent strips in opposite directions, each background and light intensity measurement is in process for the duration of a two-strip trip at a time. In practice this is in most cases a sufficient level of real-time measurement, because the changes generally take place fairly slowly in comparison with the time consumed in the measurement of the strips.

Should it be desired that the background and light source intensity measurements be carried out more frequently, both factors can always be measured at both ends of the strip.

It can also be assumed that the change in between the measurements always takes place in the same direction, in which case accuracy can be further improved by calculating an individual value for each sample by interpolating in a linear (or non-linear) fashion from the values obtained at both ends of the measurement interval.

Each measurement can be carried out so that the measurement head is momentarily stopped at each point of measurement, and the signal is integrated for a desired period in time. Thus the signal is always obtained accurately from one single spot.

The measurement can also be carried out without stopping the measurement head, which increases the speed, but the measurement area is respectively larger. The latter method is well suited for example to agglutination measurements, where each sample is subjected to measurements at several different spots.

In the device according to the invention, there is needed only one measurement channel, provided with connected optical and electronic elements. The singlechannel measurement head is also light in weight, which helps the constructing process. What is more, the measurement results are obtained sequentially, so that they are easily processed. When each sample is measured on the same channel, errors do not arise from differences prevailing in between the separate channels.

The single-channel feature and a lesser need for components are particular advantages when measuring plates provided with several tiny wells. At present, there is used, among others, a plate of the size of a microtitration plate (for instance the CLINIPLATE 384 by Labsystems Oy), containing 16×24 wells. It would be rather troublesome to construct a multichannel reader device for this type of plate, and the costs would in any case rise relatively high. The problem is further increased in that when measuring tiny wells, it is necessary to use optical elements of a higher quality, and these elements also take up more space.

By employing a steplessly movable measurement head, it is also possible to measure plates with different divisions.

When the light source intensity is measured according to the invention, there is not needed any stabilizing time for the lamp. Naturally the rise of the lamp intensity up to the level of operation takes up some time (a few seconds) after switching on, but even this time can be used for the necessary transport of the plate into the measurement chamber. The elimination of the stabilizing time speeds up the operation but also increases the service life of the lamp, reduces energy consumption and lowers the temperature inside the device. This results in lower operation costs, and the cooling of the device can be arranged in a simpler fashion.

When the background is measured according to the invention, neither a light interrupter nor a reference channel are needed. Thus the device becomes simpler. The measurement also is more reliable than in a situation where a reference channel is used.

As regards the speed of operation, the device according to the invention can be constructed to conform to the same level as multichannel devices.

In particular, the device according to the invention can be a photometer.

The measurement unit of a device for measuring optical density according to FIG. 1 comprises a sample plate 1 consisting of several well strips and placed in a measurement chamber 2 protected from external light. The measurement head 3 is provided with a branch extending to underneath the plate, said branch comprising a light focusing unit 4 for conducting light to the well above, through the transparent bottom of said well. Above the plate, there is located the second branch of the measurement head, provided with a detector unit 5 for receiving light from the well underneath. The measurement head is movable in relation to the plate, so that the plate wells are measured strip by strip. The measurement can be carried out so that the measurement head is stopped at each point of measurement, or at the same time as the measurement head is moved over the measuring spot.

The light focusing unit 4 is connected to the light source by means of a flexible photoconductor. In the focusing unit, there is created a light ray of the desired type by means of optical elements, such as lenses. In the detector unit 5, the light emitted from the well is focused on the detector by means of optical elements. The detector is provided with an amplifier for boosting the obtained signal. The amplified signal 6 is further conducted to the signal processing unit included in the device.

The plate 1 is placed in a carriage 7 supported by a frame. In the middle of the carriage, there is arranged an open area 8, in order to facilitate the measurement of the wells.

On that side of the carriage 7 that is located on the side of the measurement head 3, there is arranged an area 9 that is unobstructedly transparent to light. On the opposite side, there is arranged a light-proof area 10. Thus before or after measuring each strip, the light source intensity or the background signal can be measured. These are taken into account when calculating the measuring results of each strip.

Figure 2:
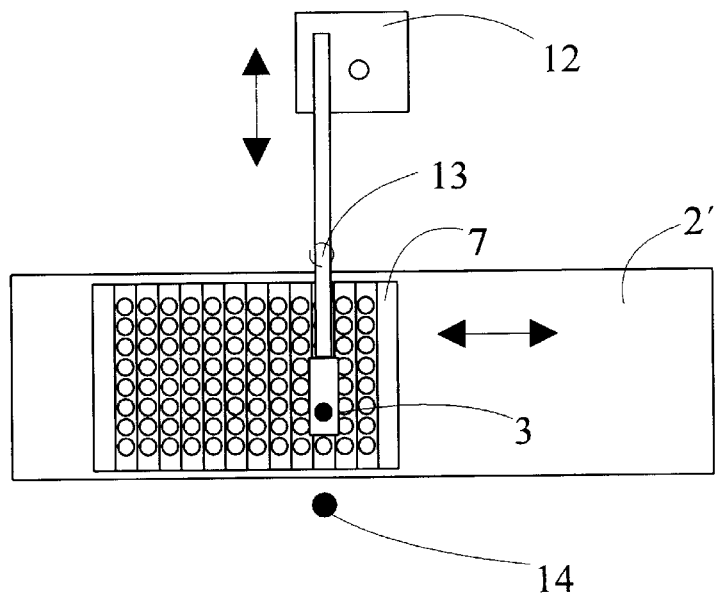
FIG. 2 is a top-view illustration of a measurement unit where both the plate and the measurement head are moved, and the background is measured at one side of the plate, and the light source intensity at the other side of the plate.

According to FIG. 2, the reader device of the plate 1 comprises a plate carriage 7 on the rail 2', said carriage being provided with means for moving the carriage in parallel to the horizontal strips. The housing of the measurement head 3 contains means 12 for moving the measurement head in parallel to the vertical strip. Moreover, the measurement chamber contains, on the measurement head trajectory, outside the plate, on one side an unobstructedly transparent area 13, and on the opposite side a light-proof area 14. In the beginning of the measurement, the measurement head is located at the first strip, for example at the transparent area, where the first value of the light source is measured. Thereafter there are measured the wells of the first strip in successive order, the measurement head is shifted to the light-proof area and the first background value is measured; simultaneously the plate is shifted so that the second strip falls at the measurement head, whereafter the second strip wells are measured in the opposite order. This sequence is repeated until all strips are measured, whereafter the measurement head is returned to the beginning.

In the device according to FIG. 2, there is described the measuring of a 8×12 plate by vertical strips. Naturally the measurement can be carried out in similar fashion by horizontal strips, too.

Figure 3:
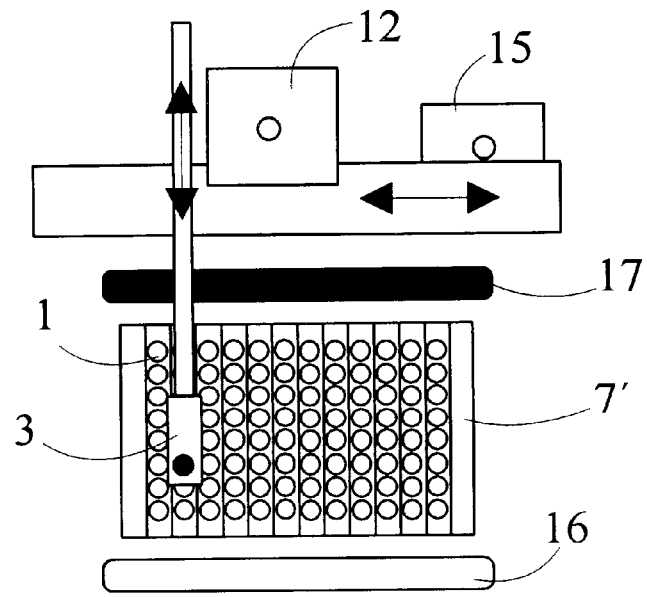
FIG. 3 is a top-view illustration of a measurement unit where the plate remains stationary and the measurement head is moved, and the background is measured at one side of the plate, and the light source intensity at the other side of the plate.

In the device according to FIG. 3, the plate 1 is in the measurement chamber placed in a stationary carriage 7', in which case the housing of the measurement head 3 includes both means 12 for moving the measurement head in the direction of the vertical strip, and means 15 for moving the head in the direction of the horizontal strip. On the other side of the plate, parallel to the horizontal strip, there is provided a transparent area 16 which is at least as long as the horizontal strip, and on the opposite side there is provided a light-proof area 17.

Figure 4:
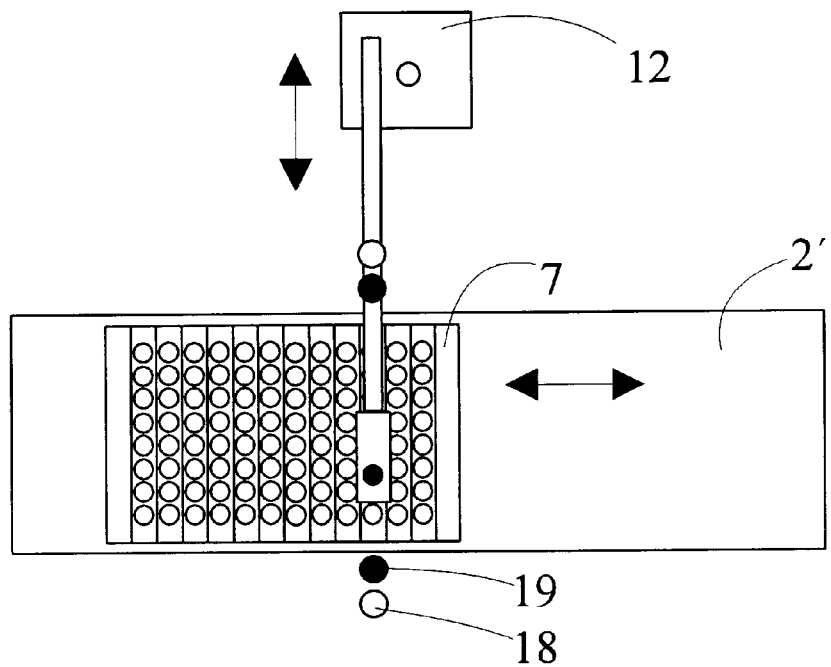
FIG. 4 is a top-view illustration of a measurement unit where both the plate and the measurement head are moved, and both the background and the light source intensity are measured at both sides of the plate.

The device according to FIG. 4 is otherwise similar to the one described in FIG. 2, except that on both sides of the plate, there are arranged both a transparent area 18 and a light-proof area 19. Thus an even higher accuracy is achieved in the measurement of the light source and the background, as both can always be measured at both ends of each strip.

Figure 5:
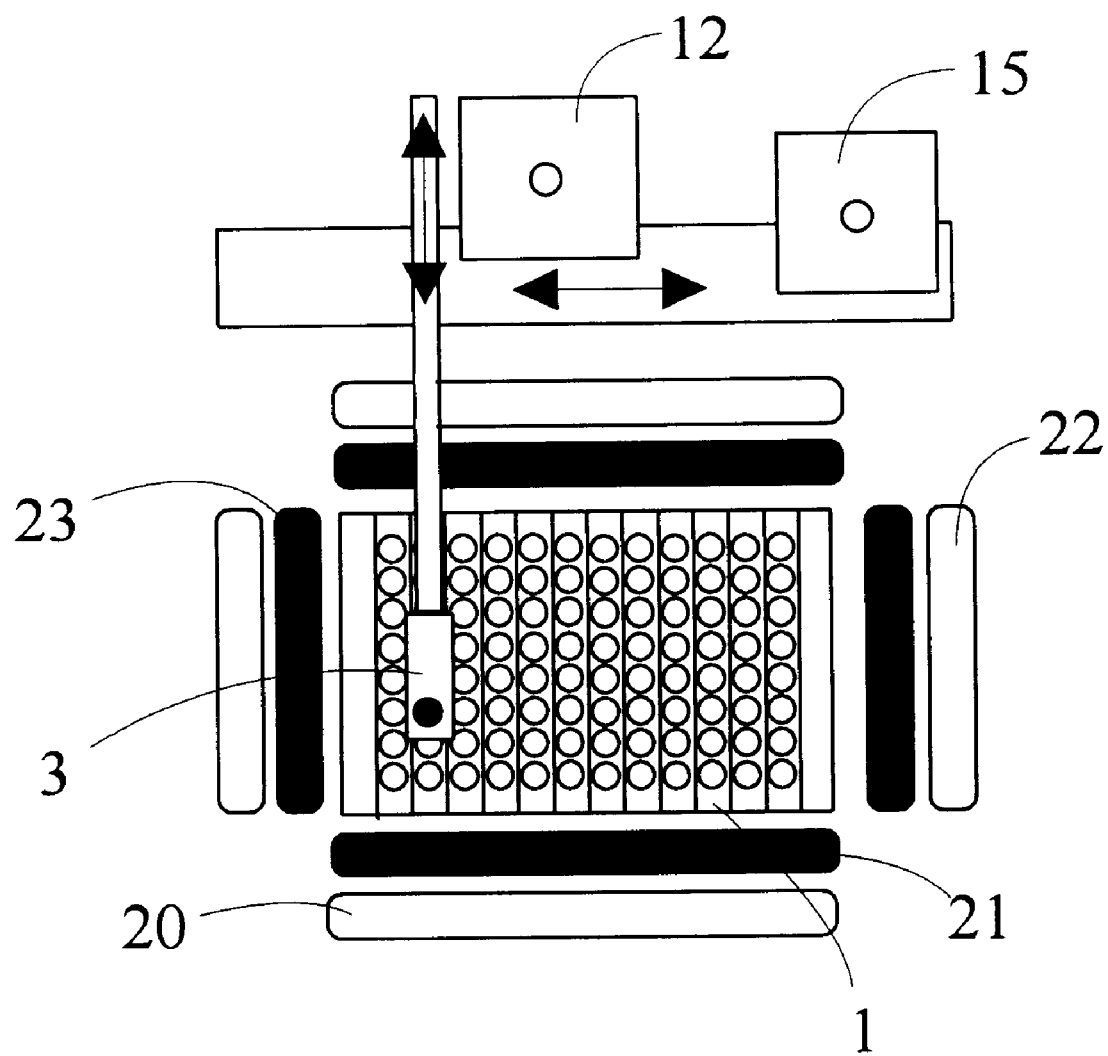
FIG. 5 is a top-view illustration of a measurement unit where the plate is stationary and the measurement head is moved, and both the background and the light source intensity are measured at both sides of the plate as well as at the end.

The device according to FIG. 5 is otherwise similar to the one described in FIG. 3, except that on both sides of the plate, there are arranged both a transparent area 20 and a light-proof area 21, and in addition to this, both ends of the plate are provided with a transparent area 22 of at least the same length as the plate end, and a light-proof area 23. Thus it is possible also to measure by horizontal strips, so that the light source and the background are measured at both ends of each horizontal strip.

Instead of a 8×12 plate, in the devices described in the drawings there can also be used parts of said plate, or one large plate or a smaller one, made with a different division, such as a plate of 16×24 wells. In that case the control system of the device can be provided with functions for reading various different plates.

When for instance the device according to FIG. 2 or 4 applies a moderate 2 g (20 m/s$^2$) acceleration and a 20 ms measurement period, the measuring of a microtitration plate takes up time as follows: shifting from well to well 4.1 s, sample measurements 1.9 s, plate transfer 2.0 s (during which time also backgrounds and light intensities are measured) and return motions from end to beginning 0.3 s, i.e. 8.3 s altogether. When applying sweep measurements, the achieved total measurement time at a rate of 0.5 m/s is about 3.3 s.

What is claimed is:

1. A device for measuring optical density of samples, the samples being placed on a plate including several strips of samples, wherein the device comprises a measurement head provided with a light source for measuring optical density by conducting light into the samples and a detector for detecting the light emitted from the samples; means for moving the measurement head and the plate in relation to each other so that the optical density of each of the samples is measured; a transparent spot and a light-proof spot outside the strips; and means for conveying the measurement head to the transparent spot for measuring light source intensity and to the light-proof spot for measuring background signal.

2. A device according to claim 1, comprising a light source for conducting light into each of the samples from one side of the sample, and a detector placed on an opposite side for detecting the light emitted from the sample.

3. A device according to claim 1 or 2, comprising means for moving the measurement head.

4. A device according to claims 3, comprising means for moving the measurement head both in parallel and transversely to a strip direction.

5. A device according to claim 1, comprising both a transparent spot and a light-proof spot provided at both ends of the strips.

6. A device according to claim 1, wherein the plate includes both vertical and horizontal strips, and wherein, outside both the vertical and horizontal strips, there is provided at least one of a transparent spot and a light-proof spot.

7. A device according to claim 1, comprising both a transparent spot at one end of the strips and a light-proof spot at an opposite end of the strips.

8. A method for measuring optical density of samples, said method comprising the steps of:
 placing samples on a plate containing several strips of several different samples,
 carrying out measurement using a measurement head and a plate, the measurement head and plate being movable in relation to each other,
 conducting light from a light source into the samples for measuring the optical density,
 detecting light emitted from the samples, and,
 outside the strips, measuring light source intensity at a transparent spot, and measuring background signal at a light-proof spot.

9. A method according to claim 8, comprising the further step of:
 on the basis of two successive light source intensity measurements, calculating corresponding values for sample measurements carried out in between.

10. A method according to claim 8, comprising the further step of:
 moving the measurement head and the plate in relation to each other during measurement.

11. A method according to claim 8, comprising the further step of:
 on the basis of two successive background signal measurements, calculating corresponding values for sample measurements carried out in between.

12. A method according to claim 9, comprising the further step of:
 on the basis of two successive background signal measurements, calculating corresponding values for sample measurements carried out in between.

13. A measurement unit of a device for measuring optical density in samples located on a plate in strips formed of several different samples, said measurement unit comprising: a measurement head for measuring optical density, with a light source to conduct light into the samples, and a detector for detecting light emitted from the samples; means for moving the measurement head and the plate in relation to each other, so that the optical density of each of the samples can be measured; outside the strip, on extensions thereof, a transparent spot and a light-proof spot; and means for conveying the measurement head to the transparent spot for measuring light source intensity and to the light-proof spot for measuring background signal.

14. A method for measuring optical density of samples, said method comprising the steps of:
 placing samples on a plate containing several strips of several different samples,
 carrying out measurement using a measurement head and a plate, the measurement head and plate being movable in relation to each other,
 conducting light from a light source into the samples for measuring the optical density,
 detecting light emitted from the samples,
 before or after measuring each strip, moving the measurement head and plate in relation to each other parallel to the strips, and,
 outside the strips, measuring at least one of light source intensity at a transparent spot and background signal at a light-proof spot.

15. A method according to claim 14, comprising the further step of:
 on the basis of two successive light source intensity measurements, calculating corresponding values for sample measurements carried out in between.

16. A method according to claim 15, comprising the further step of:
 on the basis of two successive background signal measurements, calculating corresponding values for sample measurements carried out in between.

17. A method according to claim 14, comprising the further step of:
 on the basis of two successive background signal measurements, calculating corresponding values for sample measurements carried out in between.

18. A method according to claim 15, comprising the further steps of:
 assuming that change in light source intensity is constant in direction, and,
 on that basis, calculating an individual value of light source intensity for each sample by interpolating from light source intensity measurements obtained at each end of a measurement interval.

19. A method according to claim 18, comprising the further step of interpolating values for each sample in linear fashion.

20. A method according to claim 18, comprising the further step of interpolating values for each sample in non-linear fashion.

21. A method according to claim 16 or 17, comprising the further steps of:
 assuming that change in background signal is constant in direction, and,
 on that basis, calculating an individual value of background signal for each sample by interpolating from background signal measurements obtained at each end of a measurement interval.

22. A method according to claim 21, comprising the further step of interpolating values for each sample in linear fashion.

23. A method according to claim 21, comprising the further step of interpolating values for each sample in non-linear fashion.

* * * * *